United States Patent [19]
Zook et al.

[11] Patent Number: 5,240,726
[45] Date of Patent: Aug. 31, 1993

[54] PRODUCT AND PROCESS OF MAKING LOW CALORIE NUTS

[75] Inventors: Denise Zook, Randolph; Ruth A. Yost, Mountain Lakes; Edward L. Wheeler, Fairfield; Michael S. Otterburn, Randolph; John W. Finley, Whippany, all of N.J.

[73] Assignee: Nabisco, Inc., Parsippany, N.J.

[21] Appl. No.: 893,859

[22] Filed: Jun. 5, 1992

Related U.S. Application Data

[63] Continuation-in-part of Ser. No. 731,845, Jul. 16, 1991, abandoned, and Ser. No. 804,140, Dec. 6, 1991.

[51] Int. Cl.⁵ ............................................. A23L 1/36
[52] U.S. Cl. .................................. 426/289; 426/93; 426/293; 426/309; 426/601; 426/607; 426/611; 426/632
[58] Field of Search ............... 426/607, 93, 289, 293, 426/309, 632, 601, 611

[56] References Cited

U.S. PATENT DOCUMENTS

| | | | |
|---|---|---|---|
| 2,003,415 | 10/1933 | Ammann | 426/507 |
| 2,615,159 | 10/1952 | Jackson | 426/601 |
| 2,615,160 | 10/1952 | Baur | 426/607 |
| 3,265,507 | 8/1966 | Japikse | 426/534 |
| 3,294,549 | 12/1966 | Vix | 426/632 |
| 3,645,752 | 2/1972 | Baxley | 426/632 |
| 3,740,236 | 6/1973 | Baxley | 426/632 |
| 3,772,038 | 6/1972 | Ayres et al. | 99/128 |
| 4,049,833 | 9/1977 | Gannis et al. | 426/93 |
| 4,329,375 | 5/1982 | Holloway, Jr. et al. | 426/632 |
| 4,466,987 | 8/1984 | Wilkins et al. | 426/632 |
| 5,002,802 | 3/1991 | Gannis et al. | 426/632 |
| 5,094,874 | 3/1992 | Zook | 426/632 |

FOREIGN PATENT DOCUMENTS

| | | |
|---|---|---|
| 0271963 | 12/1987 | European Pat. Off. |
| WO91/10372 | 7/1991 | PCT Int'l Appl. |
| 2007961 | 5/1979 | United Kingdom |

OTHER PUBLICATIONS

"Low Calorie Peanuts"; Vix, Spadaro, Pominski, and Pearce; Food Processing/Marketing; Sep., 1965.

"Development and Potential of Partially Defatted Peanuts"; Vix, Pominski, Pearce, and Spadaro; The Peanut Journal & Nut World; Apr., 1967.

"Procedures in Studying and Factors Influencing the Quality and Flavor of Roasted Peanuts"; Mason; Oklahoma State University; 1963.

"Food Oils and Their Uses"; Theodore J. Weiss; AVI Publishing Company, Inc.; 1983; pp. 247-268.

Primary Examiner—Helen F. Pratt

[57] ABSTRACT

The present invention relates to nuts and nut products which have at least a portion of their natural fat replaced with a low calorie fat-like material. This is achieved by partially defatting the nuts and then either contacting them or combining (i.e., mixing) them with a non-digestible or partially digestible triglyceride material which includes a triglyceride bearing one long chain fatty acid residue and two short chain fatty acid residues. The resulting nuts and nut products have the organoleptic character of full fat nuts and nut products but a much lower calorie content.

10 Claims, No Drawings

PRODUCT AND PROCESS OF MAKING LOW CALORIE NUTS

RELATED APPLICATIONS

This application is a continuation-in-part of copending application entitled "Low Calorie Nuts With The Organoleptic Character of Full Fat Nuts", Ser. No. 07/731,845, filed in the names of Holloway, Finley, and Wheeler on Jul. 16, 1991, now abandoned; and copending application entitled "Reduced Calorie Triglyceride Mixture", Ser. No. 07/804,140, filed in the names of Wheeler, D'Amelia, Leveille, Otterburn, Klemann, Finley, Roden, Chrysam, Pelloso, and Given, Jr. on Dec. 6, 1991, the disclosures of each of which are incorporated herein by reference.

BACKGROUND OF THE INVENTION

The present invention relates to nuts and nut products, and particularly to an improved process for preparing reduced calorie nuts and nut products.

The term "nuts" as used in this description includes whole nuts, splits, and pieces of nuts such as peanuts, cashews, almonds, Brazil nuts, filberts, pecans, walnuts, and the like. For purposes of conciseness in description, the following disclosure will center around the production of low-fat peanuts. It is not intended, however, to be limited to peanuts because the principles which will apply for peanuts should apply to other nuts.

The basic procedures for preparing partially defatted nuts have been known for a number of years. For example, in U.S. Pat. Nos. 2,003,415 to Ammann and 3,294,549 to Vix et al., procedures for pressing the oil from nuts such as peanuts are described. Broadly, these methods include the steps of pressing nuts until the desired quantity of fully digestible triglyceride fats are removed and then steaming or cooking the partially defatted nuts in water until the nuts are reconstituted to substantially their original size and shape.

Both the Ammann and Vix et al. patents discuss the virtues of partially defatted nuts in the diet. It is the decrease of triglyceride fat level in partially defatted nuts that give them a significantly lower calorie content than full fat nuts. Further work on the process of Vix et al. is described in a series of articles entitled, "Development and Potential of Partially Defatted Peanuts," Peanut Journal and Nut World, January and February 1967, and an article entitled, "Low Calorie Peanuts", Food Processing/Marketing, September, 1965.

Later workers, encouraged by the apparent appeal of partially defatted nuts to weight-conscious consumers, continued to work in this area. U.S. Pat. No. 3,645,752 to Baxley discloses a process which "improves" the flavor of partially defatted nuts by quenching them in a flavored oil after roasting. Although such oil quenching may improve the flavor of partially defatted nuts, it also appears to restore them to a substantially full fat content.

U.S. Pat. No. 3,740,236 also to Baxley indicates that roasted peanut flavor is reduced in proportion to the percentage of the peanut oil removed during the pressing process. Baxley, however, does not prevent flavor loss but only attempts to improve flavor after it is diminished. This is achieved by reconstituting partially defatted nuts in an aqueous binder solution containing flavor.

The reason for the loss of flavor in partially defatted nuts is not fully understood. The Doctoral Dissertation of M. E. Mason, entitled "Procedures in Studying and Factors Influencing the Quality and Flavor of Roasted Peanuts", Oklahoma State University, 1963, pages 63 and 64, indicates that the triglyceride fat pressed from peanuts contains aleurone grains, among other particulates, which appear to contain flavor precursors. The Mason dissertation, however, is not concerned with the preparation of low-fat nuts, but simply with gaining a better knowledge of the source and identification of flavor principals in peanuts.

U.S. Pat. No. 4,049,833 to Gannis et al. also recognizes the adverse effect partially defatting nuts has on flavor and texture. To correct this, Gannis contacts partially defatted nuts with a glycerol-containing solution to reconstitute them before roasting.

U.S. Pat. No. 4,329,375 to Holloway et al. discloses a process for preparing low-fat nuts, such as peanuts, which retain more of their natural flavor and texture than products prepared by earlier procedures. This high quality product is achieved by pre-roasting the nuts to partially develop a roasted nut flavor and color, pressing only after equilibration of the internal nut moisture, and limiting the amount of oil extraction.

U.S. Pat. No. 4,466,987 to Wilkins et al. relates to the production of low fat nuts prepared by moistening, initially roasting, pressing, hydrating, and finally roasting.

Although the partially defatted nuts of Gannis, Holloway, and Wilkins represent vast improvements over those products prepared simply by pressing and then cooking with hot water or steam, all such nut products inherently lack the taste and mouthfeel of full fat nuts. This problem is, at least in part, due to the lower oil content of such nuts. It is also caused by the destruction of the nut microstructure during pressing. Such structural damage is not restored by mere roasting and reconstitution. As a result, roasted, partially defatted nuts lack the crunch of full fat nuts.

SUMMARY OF THE INVENTION

The present invention relates to the preparation of nuts and nut products made from nuts which have been partially defatted, roasted, and contacted (such that absorbtion thereinto is facilitated) with a non-digestible or partially digestible triglyceride substance. As a result, the nuts and nut products have a lower calorie content than similar products made from full fat nuts, but an oily mouthfeel and, preferably, the texture of full fat nuts and products made from full fat nuts.

The roasted, partially defatted nuts can be prepared from full fat nuts in accordance with any known procedure. The partially defatted nuts are contacted or combined with a low calorie triglyceride material which includes triglycerides bearing one long chain fatty acid residue and two short chain fatty acid residues. For purposes of this application, the term "low calorie triglyceride material" is defined as a non-digestible or only partially digestible, edible triglyceride material which can replace fully digestible triglyceride fats or oils in the human diet. These materials provide the benefits of fully digestible triglyceride fats and oils—i.e., lubricity and flavor—with fewer calories. In this application, "fully digestible" shall mean that substantially all (up to 100%) of the material is digested, providing up to 9 kilocalories per gram. The term "non-digestible" shall mean that substantially all of the material is not digested by the human body and passes through the digestive system unchanged. The term "partially non-digestible"

shall encompass materials with a level of digestibility between that of non-digestible and fully digestible materials, preferably where 1.0 to 8.0 kilocalories per gram are provided.

One aspect of the invention provides that partially defatted nuts are reconstituted and contacted with the low calorie triglyceride material. The contact can be either prior to or after roasting (but preferably prior). The triglyceride material is thus infused into the partially defatted nuts. As a result, the nuts have the organoleptic character (i.e., oily mouthfeel) of full fat nuts without the calories. This occurs because of the non-digestible or partially digestible nature of the low calorie triglyceride material infusant which, unlike fully digestible triglyceride fats, passes through the human digestive system while significantly reducing the product's caloric density. It is particularly advantageous to infuse low calorie triglyceride materials which contain a relatively high level of solids at room temperature to restore added crunch to the nut.

In an alternative embodiment, the defatted nuts can be roasted and/or reconstituted in the low calorie triglyceride material as a means of contacting the nuts with the material. Still another embodiment of the invention provides that the low calorie triglyceride material be used as a glazing oil for roasted, partially defatted nuts. Moreover, any of the above embodiments can be combined as a means of contacting partially defatted nuts with a low calorie triglyceride material in order to produce nuts with lower caloric value than full fat nuts, but having the organoleptic characteristics and mouthfeel of full fat nuts. However, the infusion procedure detailed below is the preferred method of contact between the nuts and the triglyceride material.

In another aspect of the invention, roasted, partially defatted nuts are ground into a flour, and combined with (or ground together with) the low calorie triglyceride material. In this way, a nut butter product, similar to peanut butter, can be prepared and used as is, or as a filling or topping for bakery products. Additionally, the consistency and viscosity of the nut butter product can be manipulated to provide other products like "nut butter" loafs or slices. The resulting nut butter products would also have the organoleptic character of full fat nut spreads without the calories.

Advantageously, the low calorie triglyceride material contains or is combined with additives such as natural or artificial flavoring agents (preferably nut extracts), stabilizers, vitamins, and, optionally, sweeteners (artificial and/or natural).

DETAILED DESCRIPTION OF THE INVENTION

Low fat nuts and nut products with the organoleptic character of full fat nuts are produced according to the present invention by what is generally a multi-stage process. In a first stage, partially defatted nuts or a roasted, partially defatted nut flour are provided. In further stages, nuts from the first stage are contacted in one of several ways with a low calorie triglyceride material and roasted; or the roasted, defatted nut flour is combined with a low calorie triglyceride material.

The low calorie triglyceride material with which the nuts (either themselves or after having been ground) are contacted according to this invention comprise triglycerides having both long, saturated, preferably $C_{16}$ to $C_{40}$, fatty acid residues and short, preferably $C_2$ to $C_5$, acid residues. Most preferably, the long fatty acid residues will be $C_{18}$ and the short acid residues will be $C_2$ to $C_3$.

Denoting the aliphatic portion of the long fatty acid substituent as L and the short as S, the material comprises one or more SSL, SLS, LLS, and LSL species described by the following formulae:

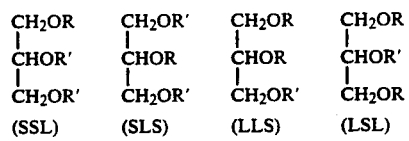

where
each R, independently, is a long chain saturated fatty acid residue having between 16 and 40 carbons, preferably 16 to 24 carbons, most preferably 18 to 22 carbons;
and
each R', independently, is a short chain acid residue having 2 to 5 carbons, preferably 2 to 4 carbons, most preferably 2 to 3 carbons.

Depending upon the preparative procedure (to be more fully described below), the materials may also contain triglycerides of the formulae

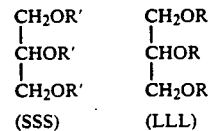

where R and R' are as defined above. However, most preferred mixtures contain essentially no SSS and preferably less than 3%, more preferably less than 1%, LLL.

As depicted above, the low calorie triglycerides employed in this invention are compounds consisting of three molecules of the same or different acids esterified to glycerol, 1,2,3-propanetriol, having the formula $(CH_2OH)_2CHOH$. The acids are short $C_2$ to $C_5$ acids, or long and saturated $C_{16}$ to $C_{40}$ acids.

One preferred embodiment is a mixture of at least two of the above described triglycerides, at least one bearing two different short residues as R' groups (SSL and SLS). Another preferred embodiment is a mixture of at least two triglyceride fats each bearing a similar array of long, saturated residues but a different complement of short chain residues.

The low calorie triglycerides are especially advantageous for nuts and nut products when they comprise at least about 50%, preferably at least about 75%, by weight SSL and SLS species and between about 0.1 and about 50%, preferably between about 5 and about 25%, by weight LLS and LSL species.

The short (volatile) acid residue, R', has no more than 5 carbons, more narrowly 2 to 4, particularly 2 or 3 carbons. R' is derived from a carboxylic acid of the formula SCOOH, where S is a short chain group such as an aliphatic or an hydroxyalkyl having 1 to 4 carbons. As denoted herein, where R' is described as having 2, 3, 4, or 5 carbons, compositions with R' groups having predominantly 2, 3, 4, or 5 carbons are included. Acylation of a glycerol hydroxyl by acid SCOOH results in the attachment of short chain S to the glycerol backbone by means of an ester linkage (—O—(CO)—). Where there is more than one R' attached to a glyceride, the R' groups may be the same or different. As used herein, the term "acid residue" refers to an acyl group comprising a short chain portion, here S and a carbonyl group, so that R'=S—(CO)—.

Short chain S may be either saturated or unsaturated (although the saturated are highly preferred), straight or branched. Short chain S may be derived from any synthetic or natural organic acid including, but not limited to acetic (ethanoic), propionic (propanoic), butyric (butanoic), valeric (pentanoic), glycolic (hydroxyacetic), lactic (2-hydroxypropanoic), hydracrylic (3-hydroxypropanoic), hydroxybutyric, hydroxypentanoic, and the like acids. As used herein, chemical names include isomeric variations; for example, "butyric acid" includes normal-butyric acid (butanoic) and iso-butyric (2-methylpropanoic) acid, "valeric acid" includes normal-valeric (pentanoic) and iso-valeric (3-methylbutanoic), and so forth. Preferred acids are acetic, propionic, and butyric acids and mixtures of these. Acetic and propionic acids are especially preferred.

Mixtures of acids may also be used, such as, for example, those derived from specific fractions of unhydrogenated, partially hydrogenated or fully hydrogenated dairy butterfat, coconut, palm kernel and the like oils. For example, butter fat has been fractionated, yielding a fraction enriched with triglycerides having 2 residues of at least 16 carbons and 1 residue with 2 to 8 carbons.

The long fatty acid residue, R, has from 16 to 40 carbons, more narrowly 16 to 24, more narrowly, 18 to 22, and even more narrowly 18 to 20 carbons. In a preferred embodiment, R has predominantly ($\geq 70\%$ or even 80%) 18 carbons (stearic acid residues). More preferably, R has $\geq 90\%$ $C_{18}$ (stearic acid residue) R groups. R is an acyl group comprising an aliphatic portion and a carbonyl, and is derived from a fatty acid of the formula LCOOH, where L is a saturated aliphatic group having 15 to 39 carbons; thus, R=L—(CO)—. Acylation of a glycerol hydroxyl by acid LCOOH results in the attachment of long chain L to the glycerol backbone by means of an ester linkage (—O—(CO)—). Where there is more than one R group attached to a glycerol backbone, the R groups may be the same or different.

R may be derived from any synthetic or natural, straight or branched saturated organic acid including, but not limited to, palmitic (hexadecanoic), stearic (octadecanoic), arachidic (eicosanoic), behenic (docosanoic), lignoceric (tetracosaenoic), cerotic (hexacosanoic), montanic (octacosanoic), melissic (triacontanoic), and the like acids. R may also be derived by hydrogenating an unsaturated acid including, but not limited to, palmitoleic (9-hexadecenoic), oleic (cis-9-octadecenoic), elaidic (trans-9-octadecenoic), vaccenic (trans-11-octadecenoic), linoleic (cis,cis-9,12-octadecedienoic), linolenic (9,12,15-octadecatrienoic and 6,9,12-octadecatrienoic), eleostearic (9,11,13-octadecatrienoic), arachidonic (5,8,11,14-eicosatetraenoic), nervonic (cis-15-tetracosenoic), eicosapentaenoic, docosatetraenoic, docosapentaenoic, docosahexaenoic, and the like acids. Chemical names include isomeric variations.

The various R groups can be mixtures of fatty acids and can be derived, for example, from non-hydrogenated, partially hydrogenated or fully hydrogenated oils such as soybean, safflower, sunflower, high oleic sunflower, sesame, peanut, corn, olive, rice bran, babassu nut, palm, mustard seed, cottonseed, poppyseed, low erucic rapeseed, high erucic rapeseed, shea, marine, meadowfoam and the like oils. Advantageously, the oils are hydrogenated, most advantageously fully hydrogenated.

Hydrogenated fats having at least about 70%, preferably at least about 75%, stearic acid residues such as hydrogenated peanut oil, hydrogenated olive oil, hydrogenated soybean oil, hydrogenated sesame oil, and hydrogenated corn oil are especially desirable for the present invention. Some embodiments employ hydrogenated fats having at least about 90% stearic acid residues, such as hydrogenated sunflower oil, hydrogenated safflower oil and hydrogenated canola.

Fatty acids derived from processed or unprocessed tallow, lard, shea butter, and dairy butter, or plant waxes such as jojoba may also be used. Specific fractions of processed or unprocessed oils, fats, or waxes may be used, and are especially advantageous in some embodiments. The oils, fats, or waxes may be hydrogenated before or after incorporation into the low calorie triglycerides used in the present invention.

The low calorie triglycerides used in this invention generally contain 33 to 67 mole % short acid residues. Fatty acid mixtures can contain amounts of medium or long, unsaturated fatty acids to the extent which these can be tolerated without unduly affecting the physical properties of the fat, or the caloric reduction. For example, some products may contain up to 20% medium and/or long, unsaturated triglycerides.

Some of the compounds used as the low calorie fatlike material used in this invention may be described by the formula

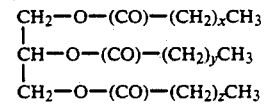

where x, y, and z = in or m
in = 0, 1, 2, or 3,
m = 16, 18, 20 or 22, and
14 $\leq$ (x + y + z) $\leq$ 47.

The long and short substituents are selected to provide a discernible fatty character in the mixtures. An advantage of the present invention is that functional properties of the fat (and, therefore, the resulting nuts and nut butter products) can be modulated by the selection of S and L groups as well as by the proportions of SSS, SLS, SSL, LLS, LSL and LLL components in the mixtures. For example, groups or components yielding high, sharply melting mixtures, stable to oxidation on storage, can be employed. In this way, the natural fats present in nuts and nut butters can be mimicked to as great an extent as possible. Particular formulations are set forth hereinafter.

The molar ratio of S to L groups in the SSS, SLS, SSL, LLS, LSL and LLL low calorie mixtures may be determined using proton or carbon nuclear magnetic resonance (hereinafter referred to as NMR), or any quantitative procedure known to those skilled in the art. The S/L ratio generally varies between 0.5 and 2.0. Using this parameter, many of the mixtures of this invention fall into one of three major groups: the first has an S/L ratio of 0.5 to 1.0; the second, 1.0 to 1.5; and the third, 1.5 to 2.0.

An advantage of the particular low calorie materials selected is that the melting point ranges can be tailored by the choice of the short and long acid residues and the amount of SSL/SLS and SLL/LSL in the mixtures. Mixtures can be further varied by adding SSS or LLL species, or conventional triglycerides.

Moreover, the choice of the short and long acid residues and the amount of SSL/SLS, SLL/LSL, SSS, LLL and conventional fats in the mixtures can be used to modulate the solids contents for fats having the same (or different) capillary melting points so that the functional properties may be further modified. By the term "solids content" is meant the percentage of a fat that exists in crystalline form at a given temperature. Solid fat contents (herein abbreviated S.F.C.) are determined using nuclear magnetic resonance according to A.O.C.S. Method Cd 16-81. Unless otherwise indicated, solid fat indices (herein abbreviated S.F.I.) are determined using dilatometry according to A.O.C.S. Method Cd 10-57. Solids percentages are reported at 50° F. (10° C), 70° F. (21.1°), 80° F. (26.7°), 92° F. (33.3°), and 100° F. (37.8° C.).

The molar percentage of SLS and LSS in the mixtures can range between 5 to nearly 100%. In some embodiments, the LSS/SLS molar percentage ranges between 50 and 100%; in others, between 75 and 100%. It is an advantage that low calorie fats containing large amounts of LSS/SLS have small amounts of L moieties.

The molar percentage of LLS and LSL in the mixtures can range from 0 to 95%. In most embodiments, the LLS and LSL molar percentage is no greater than about 50%, preferably no greater than about 25%.

The molar percentage of LLL in the mixtures is generally under 10%, more narrowly less than 5%. In some embodiments, mixtures having less than 3% LLL are preferred. In others, less than 1% is preferred. The molar percentage of SSS in the mixtures is generally under 10%; preferred mixtures contain less than 5% SSS, more narrowly less than 3%; many embodiments contain essentially no SSS or LLL species.

Based on relative proportions of S and L substituents, the low calorie triglyceride mixtures can be placed into three major groups:

Group I comprises mixtures wherein the molar ratio of short to long (S/L) substituents falls between 0.5 and 1.0. These mixtures tend to have higher capillary melting points; many embodiments melt above about 50° C., and thus are solids at room temperature.

Group II comprises mixtures wherein the molar ratio of short to long (S/L) substituents varies between 1.0 and 1.5. These mixtures tend to have mid-range melting points; many embodiments melt between about 25° and about 50° C.

Group III comprises mixtures wherein the short to long (S/L) molar ratio varies between 1.5 and 2.0. These mixtures tend to have lower melting points. Some embodiments melt below about 25° C., and are fluids at room temperature.

The Group II and Group III triglyceride mixtures are those which are most preferred for use in the present invention.

One highly preferred embodiment of this invention comprises the use of a triglyceride mixture of:

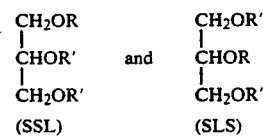

Preferred mixtures of this type contain a mixture of at least two R' groups and more SSL than SLS. Many useful compounds of this type may be described by the formula $$\begin{array}{l} CH_2-O-(CO)-(CH_2)_xCH_3 \\ CH-O-(CO)-(CH_2)_yCH_3 \\ CH_2-O-(CO)-(CH_2)_zCH_3 \end{array}$$

where x, y, and z = in or m
in = 0, 1, 2, or 3
m = 16, 18, 20 or 22, and
14 ≦ (x + y + z) ≦ 28.

One especially preferred embodiment has $x+y+z=17$.

The triglyceride mixture also generally comprises mixtures of

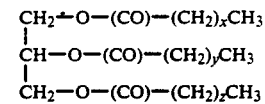

These usually have higher melting points than mixtures of SSL and SLS, especially where the LSL species predominates. Some preferred mixtures contain a mixture of two or more R groups, such as for example, R groups derived from cottonseed, soybean or fish oils; some of these contain a mixture of two or more R' groups, such as, for example a mixture of R' groups derived from acetic and propionic acid.

Many of the LLS/LSL mixtures can be described by the formula $$\begin{array}{l} CH_2-O-(CO)-(CH_2)_xCH_3 \\ CH-O-(CO)-(CH_2)_yCH_3 \\ CH_2-O-(CO)-(CH_2)_zCH_3 \end{array}$$

where x, y, and z = in or m
in = 0, 1, 2, or 3,
m = 16, 18, 20 or 22, and
29 ≦ (x + y + z) ≦ 46.

Component triglycerides making up the low calorie fat mixtures may be prepared using synthetic procedures known to those skilled in the art, such as, for example, directly esterifying glycerol or glycerol esters with fatty acids, fatty acid halides (notably chlorides) or fatty acid anhydrides, transesterifying glycerol with fatty acid esters, or interesterifying long and short chain triglycerides for such time and under such conditions that triglycerides bearing long and short residues form. Starting materials for triglyceride preparations may be obtained commercially or isolated from natural sources. Alternatively, component triglycerides may be isolated from natural or processed fats or oils, or fractions thereof, as discussed above.

Some desirable triglyceride mixtures are prepared using a random interesterification of triacetin, tripropionin and/or tributyrin with a substantially hydrogenated fat having at least about 70%, in some cases at least about 75%, more preferably at least about 90%, stearic acid residues. An advantage is that the preparative procedure for many mixtures can be facilitated by employing at least two triglycerides bearing only short triglycerides. For example, because of solubility differences, triacetin reacts sluggishly with hydrogenated canola, but in the presence of tripropionin, the reaction is facilitated.

The low calorie triglycerides may be combined with the nuts either alone, or in combination with another fat and/or fat mimetic. Other fats include natural triglycerides rich in highly desirable or essential fatty acids, such as oleic, linoleic, linolenic, or eicosapentaenoic acid, triglycerides bearing fatty acids having beneficial attributes such as those associated with conjugated linoleic acid isomers, medium chain triglycerides and the like. Other fat mimetics include any heretofore suggested as edible fat replacements, including, but not limited to, sugar esters including sucrose polyesters, neoalkyl esters, polyglycerol esters, malonate esters, propoxylated glycerols, retrofats, carboxy/carboxylates, polyvinyl alcohol esters and the like.

The following is a list of representative, but not limiting, low calories triglycerides which may be employed in the mixture used in this invention:

2-Butyryl-1,3-distearoyl Glyceride (1)
$CH_2-O-(CO)-(CH_2)_{16}CH_3$
$CH-O-(CO)-(CH_2)_2CH_3$
$CH_2-O-(CO)-(CH_2)_{16}CH_3$ 1,2-Dibutyryl-3-stearoyl Glyceride (2)
$CH_2-O-(CO)-(CH_2)_2CH_3$
$CH-O-(CO)-(CH_2)_2CH_3$
$CH_2-O-(CO)-(CH_2)_{16}CH_3$ 1-Butyryl-2,3-distearoyl Glyceride (3)
$CH_2-O-(CO)-(CH_2)_2CH_3$
$CH-O-(CO)-(CH_2)_{16}CH_3$
$CH_2-O-(CO)-(CH_2)_{16}CH_3$ 1,3-Dibutyryl-2-stearoyl Glyceride (4)
$CH_2-O-(CO)-(CH_2)_2CH_3$
$CH-O-(CO)-(CH_2)_{16}CH_3$
$CH_2-O-(CO)-(CH_2)_2CH_3$ 2-Isobutyryl-1,3-distearoyl Glyceride (5)
$CH_2-O-(CO)-(CH_2)_{16}CH_3$
$CH-O-(CO)-CH(CH_3)_2$
$CH_2-O-(CO)-(CH_2)_{16}CH_3$ Tristearoyl Glyceride (6)
$CH_2-O-(CO)-(CH_2)_{16}CH_3$
$CH-O-(CO)-(CH_2)_{16}CH_3$
$CH_2-O-(CO)-(CH_2)_{16}CH_3$ Tributyryl Glyceride (7)
$CH_2-O-(CO)-(CH_2)_2CH_3$
$CH-O-(CO)-(CH_2)_2CH_3$
$CH_2-O-(CO)-(CH_2)_2CH_3$ 1-Arachidoyl-2,3-dipropionyl Glyceride (8)
$CH_2-O-(CO)-(CH_2)_{18}CH_3$
$CH-O-(CO)-CH_2CH_3$
$CH_2-O-(CO)-CH_2CH_3$ 1,2-Dipalmitoyl-3-valeryl Glyceride (9)
$CH_2-O-(CO)-(CH_2)_{14}CH_3$
$CH-O-(CO)-(CH_2)_{14}CH_3$
$CH_2-O-(CO)-(CH_2)_{14}CH_3$ 2-Propionyl-1,3-distearoyl Glyceride (10)
$CH_2-O-(CO)-(CH_2)_{16}CH_3$
$CH-O-(CO)-CH_2CH_3$
$CH_2-O-(CO)-(CH_2)_{16}CH_3$ 1-Acetyl-2-propionyl-3-stearoyl Glyceride (11)
$CH_2-O-(CO)-CH_3$
$CH-O-(CO)-CH_2CH_3$
$CH_2-O-(CO)-(CH_2)_{16}CH_3$ 1-Acetyl-2-butyryl-3-stearoyl Glyceride (12)
$CH_2-O-(CO)-CH_3$
$CH-O-(CO)-(CH_2)_2CH_3$
$CH_2-O-(CO)-(CH_2)_{16}CH_3$ 1-Butyryl-2-palmitoyl-3-stearoyl Glyceride (13)
$CH_2-O-(CO)-(CH_2)_2CH_3$
$CH-O-(CO)-(CH_2)_{14}CH_3$
$CH_2-O-(CO)-(CH_2)_{16}CH_3$ 1-Behenoyl-2-butyryl-3-stearoyl Glyceride (14)
$CH_2-O-(CO)-(CH_2)_{20}CH_3$
$CH-O-(CO)-(CH_2)_2CH_3$
$CH_2-O-(CO)-(CH_2)_{16}CH_3$ 1-Palmitoyl-2-propionyl-3-stearoyl Glyceride (15)
$CH_2-O-(CO)-(CH_2)_{14}CH_3$
$CH-O-(CO)-CH_2CH_3$
$CH_2-O-(CO)-(CH_2)_{16}CH_3$ 1-Palmitoyl-2,3-distearoyl Glyceride (16)
$CH_2-O-(CO)-(CH_2)_{14}CH_3$
$CH-O-(CO)-(CH_2)_{16}CH_3$
$CH_2-O-(CO)-(CH_2)_{16}CH_3$ 1,2-Dipalmitoyl/stearoyl-3-valeryl Glyceride (17)
$CH_2-O-(CO)-(CH_2)_3CH_3$
$CH-O-(CO)-L$
$CH_2-O-(CO)-L$
where the L's comprise a mixture of 90-97% $-(CH_2)_{16}CH_3$ and 3-10% $-(CH_2)_{14}CH_3$ 2-Acetyl/propionyl-1,3-distearoyl Glyceride (18)

-continued

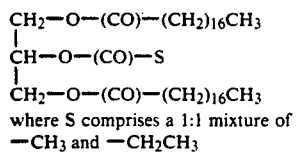

where S comprises a 1:1 mixture of
—CH₃ and —CH₂CH₃

2-Lactoyl-1,3-distearoyl Glyceride (19)

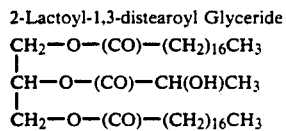

2-Butyryl-1,3-di(10-methyl)stearoyl Glyceride (20)

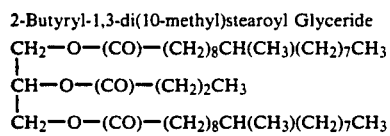

1-Isobutyryl-3-(10-methyl)stearoyl-2-stearoyl Glyceride (21)

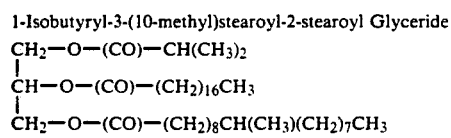

Other nonlimiting examples of component triglycerides so derived include compounds of the formula:

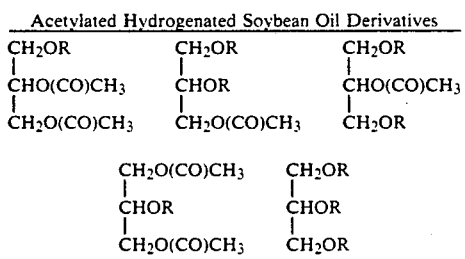

where the R groups are derived from hydrogenated soybean oil.

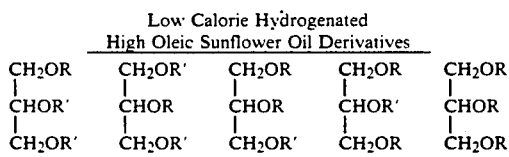

where R' is a mixture of —(CO)—CH₃ and —(C-))—(CH₂)₂CH₃ and the R groups are derived from hydrogenated high oleic sunflower oil.

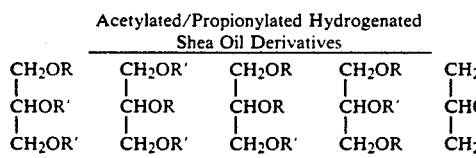

where R' is a mixture of —(CO)—CH₃ and —(-CO)—CH₂CH₃, and the R groups are derived from hydrogenated shea oil and the like.

In a preferred embodiment, at least some of the low calorie triglycerides in the mixture bear mixtures of at least two short chain acid residues. Preferred mixtures are acetic and propionic acid residues, acetic and butyric acid residues, propionic and butyric acid residues, and acetic, propionic, and butyric acid residues.

In another preferred embodiment, at least some of the low calorie triglycerides in the mixtures are mixtures of at least two triglycerides bearing long, saturated residues but different complements of short chain groups. Thus, mixtures of at least two triglycerides bearing acetic acid residues or propionic acid residues or butyric acid residues or a mixture of acetic acid and propionic acid residues, or a mixture of acetic acid and butyric acid residues, or a mixture of propionic acid residues and butyric acid residues, or a mixture of acetic acid, propionic acid, and butyric acid residues with long, saturated residues are encompassed. Preferred combinations of this type are mixtures containing at least two triglycerides, each bearing acetic, propionic or butyric acid residues and long, saturated residues.

The low calorie triglyceride materials used herein should be essentially trans-free using A.O.C.S. Method Cd 14-61 and beta crystal free. Moreover, they should have the following physical properties:

a Mettler Drop point of about 29° C. to about 41° C. using A.O.C.S. Method Cc 18-80;

a smoke point of no less than about 250° F., and preferably no less than about 375° F., using A.O.C.S. Method Cc 9a-48;

a flash point of no less than about 420° F., and preferably no less than about 460° F., using A.O.C.S. Method 9a-48;

a fire point of no less than about 420° F., and preferably no less than about 460° F., using A.O.C.S. Method 91-48;

a refractive index at 60° C of about 1.4250 to 1.4770 using A.O.C.S. Method Cc 7-25;

a saponification value of at least about 170, and preferably at least about 185, using A.O.C.S. Method 3-25;

an oxidation stability using A.O.C.S. Method Cd 12-57 for at least about 270 hours;

a free fatty acid value of about 0.15 to 0.60% using A.O.C.S. Method 5a-40;

a viscosity of about 50 to about 95 cps at 68° F., about 25 to about 42 cps at 100° F., and about 14 to about 23 cps at 150° F.; and essentially no crystals exceeding 8μ observed on microscopic examination under polarized light.

To be useful for the preparation of low calorie nuts or nut butter products according to this invention, the fat-like materials chosen should have the following solid fat index:

| Temperatures | Solids (%) |
|---|---|
| 50° F. | at least 35 |
| 70° F. | at least 20 |
| 80° F. | 5 to 40 |
| 92° F. | 2 to 25 |
| 100° F. | 0 to 15 | more narrowly the following

| Temperatures | Solids (%) |
|---|---|
| 50° F. | at least 40 |
| 70° F. | at least 25 |
| 80° F. | 5 to 30 |
| 92° F. | 2 to 20 |
| 100° F. | 0 to 10 |

The preparation of partially defatted nuts in the first stage can be carried out by any one of several processes. For example, any of the processes of Ammann, Vix, Gannis, Holloway, or Wilkins, all of which are hereby incorporated by reference, can be used. Moreover, the processes taught by Gannis et al. in U.S. Pat. No. 5,002,802 and Zook in U.S. Pat. No. 5,094,874 (the disclosures of each of which are also incorporated by reference herein) for preparing partially defatted nuts can be employed.

Partially defatted nuts may be prepared by mechanically pressing raw nuts to extract at least about 30%, and most commonly about 40% to about 52%, of their initial oil content. This can be achieved, for example, by employing a Carver Press at applied pressures of greater than about 1,000 pounds per square inch (psi) for about 15 to about 120 minutes. Although the exact times and pressures for oil extraction can be varied to obtain the desired degree and rate of extraction, pressures of no greater than about 1,500 psi, particularly about 1,100 to about 1,300 psi, are preferred. Although pressures above this range will extract oil more rapidly, more physical damage to the nuts and possibly a reduction in the amount of retained natural flavors can occur. Although pressures below the disclosed range can be employed with somewhat less nut breakage, the time required for extraction of the desired amount of oil will increase. By utilizing the above-described pressing conditions, a desirable balance between calorie reduction and final product flavor and texture can be achieved with oil reduction of between about 40% and about 52%. Preferably, the pressure is elevated to the desired level as quickly as possible.

Recently, the preparation of defatted nuts having more of their oil extracted has become feasible. Such nuts have up to about 75% of their initial oil content extracted, and sometimes even more. It is not impossible for defatted nuts having over 80% of their initial oil content removed to be prepared. As used herein, therefore, the term "partially defatted nuts" will refer to nuts which have had at least some of their initial oil content removed, generally at least about 30% and, more narrowly, about 40% to about 80% removed.

After pressing, the nuts are flat and undesirably dense. It is, therefore, appropriate to expand (or reconstitute) the nuts to bulk densities which approximate those of full fat nuts (however, when nut butter products are desired, reconstitution is not necessary since the defatted nuts are ground into flour).

The bulk densities sought when low fat nut products are to be prepared will generally approach about 0.40 grams per cubic centimeter (g/cc) (determined, for instance, by filling a 500 cubic centimeter graduated cylinder with nuts, determining the weight of the nuts, and dividing the weight in grams by the volume in cubic centimeters). Preferably, the bulk density of the reconstituted nuts is within the range of about 0.32 to about 0.39 g/cc.

Expansion can be effected by contacting the defatted nuts with sufficient water to reconstitute them when subsequently roasted. Such contact is preferably at a level of about 3 to about 7, more preferably about 4, pounds of water per hundred pounds of nuts. In an alternate embodiment, the nuts can be reconstituted at the same levels in the low calorie triglyceride material infusant described hereinbelow, in order to provide the desired contact with the material, which will be absorbed into the nuts. This can be the sole contact between the material and the nuts, or it can be used in addition to other contact methods detailed herein. The water or infusant and nuts may be contacted in any suitable mixing device such as a rotatable coating drum.

Alternatively, the nuts can be reconstituted using steam. Although pressurized steam can be employed for reconstitution, steam at atmosphere pressure has been found to be effective and is preferred. The use of steam or pressurized steam may have economic disadvantages when compared with merely contacting the nuts with water, because of the additional capital outlay, etc. However, it has been found that nuts reconstituted in this manner exhibit superior texture and flavor after roasting. The exact reason for this is unknown, but it is believed steam or pressurized steam reconstitution opens the pores of the nuts more effectively, which leads to the observed improvements on roasting. These improvements may justify the additional capital outlay, etc. involved with steam-mediated reconstitution.

When steam or pressurized steam is used to reconstitute the nuts, the nuts are contacted with the steam in a suitable vessel, such as a rotatable coating drum when steam at atmospheric pressure is used, or a pressure cooker or steam chamber when pressurized steam is used. Contact with the steam should continue for a time sufficient to achieve satisfactory reconstitution. Advantageously, steam reconstitution proceeds for about 30 seconds to about five minutes, more preferably about 45 seconds to about four minutes, to ensure a desirable level of reconstitution.

When whole nuts (which term is intended to include splits and pieces as noted above) are desired, the nuts are roasted and contacted with the low calorie fat-like material (if reconstitution contact is not employed or not intended to be the sole contact mechanism). The particular order in which these operations is effected depends on the practitioner. Contact after roasting will produce satisfactory low calorie nuts. However, it is preferred that contact be prior to roasting when infusion contact with the low calorie triglyceride material is desired, for closest approximation of full fat nuts.

Infusion contact between reconstituted, partially defatted nuts and low calorie triglyceride material can be carried out in any number of ways. One technique is to immerse the partially defatted nuts in a bath of low calorie triglyceride materials, causing the nuts to absorb relatively large amounts of the triglyceride material. Except when incorporating heat sensitive substances in the triglyceride material, the nuts can be contacted with fatty material while still hot from roasting (when postroast techniques are employed). Preferably, the low calorie triglyceride material is relatively cool (i.e., about 40° F. to about 150° F., preferably about 65° F. to about 110° F.) during such contact.

Alternatively, where it is desired to limit the amount of triglyceride material infused into the nuts, giving them a less oily character, they can be contacted with a relatively small quantity of triglyceride material by spraying, tumbling, or any conventional coating technique. As a result, only that limited quantity of fatty material is capable of being infused into the nuts. The quantity of triglyceride material utilized in the latter embodiment is about 5 to about 15, preferably about 10, pounds per 100 pounds of nuts.

In the infusion operation, both the nuts and the oil can be at relatively high temperatures, i.e., about 180° F. to about 320° F. Preferably, however, both the nuts and the infusant are at room temperature for effective infusion. It is desirable, but not critical, that both the nuts and the triglyceride material are at approximately the same temperature. An acceptable product is produced when the triglyceride material is at a lower temperature than the nuts or the nuts are at a lower temperature than the triglyceride material, although the latter situation may be less preferred.

When both the nuts and the triglyceride material are at relatively low temperatures, i.e., room temperature, contacting the nuts with the edible triglyceride material may cause the triglyceride material to solidify on the surface of the nuts (depending on the melting temperature of the triglyceride material). When this occurs, the nuts can be warmed to a temperature sufficient to melt the triglyceride material (usually 220° F. is sufficient) which will cause the triglyceride material to infuse into the nuts.

Advantageously, the triglyceride material contains a flavoring agent which is incorporated into the nuts. Suitable flavoring agents include nut flavor concentrates which are naturally present in nuts or nut oil. Such materials can be obtained by a variety of conventional techniques (e.g., dark roasting nuts and then extracting the nut oil). These nut flavor concentrates can be recovered from nuts which are either the same as or different from the partially-defatted nut being infused.

Other flavoring agents include: fruit flavors, chocolate or other confectionery flavors; mint flavor; honey flavor, the flavor of alcoholic beverages such as beer, wine, and whiskey; and other desired artificial or natural flavor, and mixtures thereof.

In addition, the flavoring agents can be encapsulated by known techniques for a superior flavor note. Moreover, encapsulation will also serve to protect flavoring agents which may be sensitive to handling or otherwise subject to degradation during the infusion operation or storage of the resulting nuts. Such agents include artificial sweeteners, such as aspartame, and fat soluble vitamins, such as vitamins A, D, and E.

Additionally, other desired additives such as texturizers may be included in the triglyceride material infusant. Suitable texturizers include fiber, especially pea fiber, bulking agent such as methylcellulose, and corn syrup solids. These texturizers assist in the formation of a finished product having a texture and color more nearly that of full-fat nuts.

The triglyceride material and any other additives are mixed in a suitable vessel by conventional means. Infusion can then be effected by any conventional technique. For example, spraying a controlled amount of fat onto moving nuts in a continuous coating drum for a period of time sufficient to allow infusion of edible oil and any additives to a level of about 2% to about 10% by weight of the nuts. Typically, infusion is carried out for about one minute to about five minutes, more preferably about two minutes to about four minutes.

In an alternative embodiment, infusion is achieved by differential pressure. This is carried out by drawing a vacuum on the roasted, partially defatted nuts prior to contact with the low calorie triglyceride material. Vacuum should be drawn at a level of about 20 to about 35 in. Hg., more preferably about 25 to about 30 in. Hg. While the nuts are still under vacuum, they are contacted with the triglyceride material, preferably by spraying. The vacuum is held for at least about seven minutes, more preferably at least about nine minutes, and then broken. Afterwards, the nuts should be held for from up to about 1 hour to about 8 hours, or subjected to pressure (i.e., about about 10 to about 50 psi, more preferably about 15 to about 40 psi) for about 2 to about 5 minutes to aid infusion.

After having been defatted, and reconstituted when appropriate, the nuts are roasted. As noted above, roasting can be before, but is more preferably after, infusion. The roasting process is preferably dry roasting (i.e., roasting in the substantial absence of added oil, usually less than 10% by weight of the nuts, and most preferably none), although oil roasting can also be effected.

The nuts are dry roasted in any suitable manner that gives them the characteristic taste and texture of roasted nuts. Typically, the nuts are roasted to a moisture content of less than about 3%, preferably less than about 2%, and most preferably about 1.5% or less. The degree to which the nuts are roasted should correspond to an Agtron color photometer reading of about 60 to about 95 in the green mode with 12% and 33% plates defining the reading scale. Most preferably, the reading will be within the range of about 80 to about 90.

In air roasting, the nuts are roasted in a stream of hot air at a temperature of about 275° F. to about 400° F., advantageously about 320° F. to about 335° F. Roasting times and temperatures can be varied depending upon the particular type of nut being processed, as well as the roasting temperature and degree of roasting desired. Illustratively, the time and extent of roasting will be greater for peanuts (i.e., about 10 minutes to about 30 minutes) than for cashews (i.e., about 3 minutes to about 15 minutes). The most appropriate conditions to be adopted in any particular instance can be readily determined by the skilled artisan.

In granular roasting, the nuts are contracted with a finely divided heat transfer media which is heated to a temperature of about 315° F. to about 465° F., preferably about 380° F. to about 410° F. Roasting times and temperatures will vary depending upon the particular type of nut being processed and the degree of roasting desired. Illustratively, the time and extent of roasting will be greater in the case of peanuts (i.e., about 1 minute to about 9 minutes), than in the case of cashews (i.e., about 30 seconds to about 3 minutes).

The finely divided heat transfer media can be any suitable finely divided material which will absorb heat from a heat source, such as a flame, and transfer the heat to the nuts upon contact. Preferably, the finely divided heat transfer media is salt, ceramic beads, sand, or metal balls, and is most preferably ceramic beads.

When oil roasting, typically, the nuts are roasted in an edible oil such as refined peanut oil at a temperature in the range of about 300° F. to about 330° F., preferably from about 315° F. to about 325° F., and for a time which will vary depending upon the particular type of nut being processed and upon the temperature of roasting and the degree of roasting desired. The oil roasting can also be effected in a bath of low calorie triglyceride material where the material has sufficiently high flash and fire points to permit roasting temperatures to be achieved (a sufficiently high smoke point is also preferred, but is primarily for the sake of convenience). Roasting in this material can comprise the only contact between the low calorie triglyceride material and the nuts, into which the material is absorbed, or it can be combined with other contact procedures.

Illustratively, the time and extent of roasting will be greater in the case of peanuts (from about 4.5 to about 7 minutes) than in the case of cashews (from about 1.5 to about 3.5 minutes). The most appropriate roasting conditions to be adopted in any particular instance can be determined readily by the skilled artisan.

After roasting and infusion, the nuts may be glazed with an oil or the low calorie triglyceride material (as one of the contact methods intended to be included herein). They can also be coated with various powdered flavoring agents such as allspice, cinnamon, clove, caraway, bay, sage, ginger, basil, and the like. These materials can be employed alone or with condiments such as salt, pepper, monosodium glutamate, and the like. In addition, texturizers such as, glycerine and polypropylene glycol, and binders such as, natural gums, dextrins, gelatin, sugars, and the like, can be applied.

Desirable solid fat index ("SFI") profile values for the low calorie triglyceride material used for contact with (such as infusion into) nuts are in the following ranges:

| Temperatures | Solids (%) |
| --- | --- |
| 50° F. | at least 45 |
| 70° F. | at least 30 |
| 80° F. | 15 to 25 |
| 92° F. | 5 to 20 |
| 100° F. | 0 to 10 |

More preferably,

| Temperatures | Solids (%) |
| --- | --- |
| 50° F. | 60 to 80 |
| 70° F. | 55 to 75 |
| 80° F. | 50 to 70 |
| 92° F. | 5 to 15 |
| 100° F. | 0 to 5 |

One preferred triglyceride material is prepared by randomly interesterifying, using a reactant molar ratio of 11:1:1, triacetin, tripropionin and hydrogenated soybean oil and then steam deodorizing.

This material is essentially trans-free using A.O.C.S. Method Cd 14-61 and beta crystal free and has the following physical properties:
 a Mettler Drop point of about 35.5° F. using A.O.C.S. Method Cc 18-80;
 a smoke point of about 295° F. using A.O.C.S. Method Cc 9a-48;
 a flash point of about 465° F. using A.O.C.S. Method 9a-48;
 a fire point of about 500° F. using A.O.C.S. Method 91-48;
 a free fatty acid value of about 0.46% using A.O.C.S. Method 5a-40;
 an S.F.C. of about 89.1% at 50° F., about 86.7% at 70° F., about 82.8% at 80° F., about 23.2% at 92° F., and about 0% at 100° F. using A.O.C.S. Method Cd 16-81;
 an S.F.I. of about 69.7% at 50° F., about 68.75% at 70° F., about 63.9% at 80° F., about 10.11% at 92° F., and about 0% at 100° F. using A.O.C.S. Method Cd 10-57;
 a viscosity of about 36.2 cps at 100° F. and about 19.7 cps at 150° F.;
 a Lovibond Color of about 8.2 Red/68 yellow using a 1 inch column following A.O.C.S. Method Cc 136-45;
 a molar ratio of short to long substituents of 1.7; and essentially no crystals exceeding 8μ observed on microscopic examination under polarized light.

Another preferred material is prepared by randomly interesterifying, using a reactant molar ratio of 2.5:1, tributyrin and hydrogenated soybean oil and then steam deodorizing. This low calorie triglyceride material is more fully described below, where it is included in a nut butter product of this invention.

In making a nut butter product, as opposed to the whole, split, or pieces of nuts described above, a defatted nut flour is provided. In this case, there is no need for reconstitution of the nuts after they have been defatted, since the defatted nuts (which have preferably been roasted as described above) are to be ground into nut flour. The grinding of the defatted nuts should be sufficient to form a nut flour having an average particle size which is no greater than about 250 microns. More advantageously, the average particle size can vary between about 10 and about 100 microns. The defatted nuts can be ground by conventional apparatus to prepare the nut flour.

The defatted nut flour is then combined, such as by blending, with the low calorie triglyceride material(s) described above to form a nut butter product. The particular low calorie triglyceride material is chosen to provide a nut butter product having the desired consistency and viscosity. For instance, if the nut butter product sought is one to be used as an injectable filling for a baked product like a cookie, the nut butter product should be somewhat more fluid. If, on the other hand, the nut butter product sought is a loaf from which slices of nut butter or any several desirable shapes of creatures or animals can be made, then the product should be more plastic. Other nut butter products having different degrees of spreadability, for instance for toppings or icings, can be prepared having consistency which vary between that for an injectable filling and a sliced product.

The consistency of the nut butter products may be measured with the aid of an penetrometer employing a coneshaped aluminum needle having the following characteristics:
 Angle, 90°.
 Maximum diameter, 3.2 cm.
 Total weight, 78.3 grams including cone, shaft and 50 grams
 wt. according to A.S.T.M. method D217-52T.

In actual test the needle is brought to the surface of the sample, released for 5 seconds, and the penetration in tenths of a millimeter is read from a dial indicator.

For a fluid, injectable product, the desired range of penetration should be above about 300 and is preferably about 350 to about 450. When a loaf or sliced product is sought, the range of penetration should be below about 200 and is preferably about 50 to about 150. A nut butter product having the consistency of conventional peanut butter should exhibit a range of penetration between about 200 and about 300.

In order to effectively control the consistency of the nut butter product such that any desired consistency and viscosity can be obtained, it is preferable to use a mixture of low calorie triglyceride materials, one having a lower viscosity, and another having a higher viscosity. By combining these two materials, different viscosities can be achieved in a resulting nut butter product. One way this can be accomplished is by preparing a low calorie triglyceride material for use itself and then fractionating that low calorie triglyceride material to separate a liquid and a hardstock fraction. The liquid fraction can be recovered and combined with the parent material in various manners to achieve a desired consistency and viscosity for the resulting nut butter product.

For instance, if an injectable, fluid nut butter product is desired, a 1:1 weight ratio of liquid low calorie triglyceride fraction and parent low calorie triglyceride material may be used to prepare the nut butter product. However, if a plastic slice product is desired, a 3:1 ratio of parent low calorie triglyceride material to liquid low calorie fat fraction may be more appropriate. The skilled artisan will recognize that, depending on the specific characteristics of the low calorie triglyceride materials employed, different ratios of one to the other will be appropriate depending on the final product.

It will also be recognized that the preparation of a low calorie triglyceride material having the characteristics necessary for the production of a nut butter product by itself is possible and may eliminate the need for the combination of a liquid and a solid low calorie triglyceride material.

Desirable SFI profile values for the low calorie triglyceride materials used for preparing nut butter products using roasted, defatted nut flour are in the following ranges:

| Temperatures | Solids (%) |
| --- | --- |
| 50° F. | at least 45 |
| 70° F. | at least 25 |
| 80° F. | 5 to 20 |
| 92° F. | 2 to 15 |
| 100° F. | 0 to 10 |

More preferably,

| Temperatures | Solids (%) |
| --- | --- |
| 50° F. | 55 to 75 |
| 70° F. | 40 to 75 |
| 80° F. | 9 to 16 |
| 92° F. | 5 to 12 |
| 100° F. | 0 to 7 |

One preferred triglyceride material is prepared by randomly interesterifying, using a reactant molar ratio of 2.5:1, tributyrin and hydrogenated soybean oil and then steam This material is essentially trans-free and has the following physical properties:

a Mettler Drop point of about 33.2° F. using A.O.C.S. Method Cc 18-80;

a smoke point of about 290° F. using A.O.C.S. Method Cc 9a-48;

a flash point of about 510° F. using A.O.C.S. Method 9a-48;

a fire point of about 545° F. using A.O.C.S. Method 91-48;

a free fatty acid value of about 0.23% using A.O.C.S. Method 5a-40;

an S.F.C. of about 83.4% at 50° F., about 41.5% at 70° F., about 11.2% at 80° F., about 7.7% at 92° F., and about 6.3% at 100° F. using A.O.C.S. Method Cd 16-81;

an S.F.I. of about 66.83% at 50° F., about 36.93% at 70° F., about 12.23% at 80° F., about 7.69% at 92° F., and about 6.87% at 100° F. using A.O.C.S. Method Cd 10-57;

a Lovibond color of about 5.8 Red using a 1 inch column following A.O.C.S. Method Cc 136-45;

a viscosity of 19.7 cps at 150° F.;

a molar ratio of short to long substituents of 1.17; and essentially no crystals exceeding $8\mu$ observed on microscopic examination under polarized light.

In addition, as noted, the nut butter product triglyceride materials can be separated, or fractionated, into liquid and hardstock fractions. The liquid fraction can then be collected and combined with the parent triglyceride material. In this way, combining the two in differing weight ratios provides a great deal of flexibility in final product consistency. The fractionation of the triglyceride material yields a liquid fraction having a molar ratio of short to long substituents of 1.44.

The nut butter product of the present invention comprises partially defatted nut flour in amounts up to about 55% by weight, and preferably about 37% to about 45%. However, it is not necessary that all the nut flour used in the nut butter product have the same level of oil. In fact, nut flour which has been defatted in a conventional manner to remove about 40% to about 52% of the oil can be combined with nut flour defatted to a greater extent—up to about 80% of the oil removed and higher, or either can be used alone. The triglyceride material(s) should be present in amounts up to about 35% by weight, preferably about 20% to about 27%.

In addition, other components may also be included in the nut butter product, including a stabilizer such as partially hydrogenated vegetable oils with polyglycerol esters of fatty acids, commercially available as Durasorb D, from Loders & Croklaan of Lisle, Illinois, as well as other art recognized peanut butter stabilizers which can be present in amounts from about 1% to about 5% by weight. Other components include polydextrose, present to improve spreadability, as well as to provide better flavor impact, mouthfeel, and product stickiness, present at about 11% to about 18% by weight. In addition, sweeteners such as sugar in amounts between about 3% and about 20% by weight or artificial sweeteners like Aspartame, saccharine, and other art recognized sweeteners can also be included as well as flavorants such as non-fat dry milk and/or salt.

After the ingredients are blended together, they are preferably ground in a device such as an Attritor 01 by Union Process of Akron, Ohio, typically at about 500 r.p.m. for about 15 minutes. After grinding, the product is quiescently cooled to allow formation of crystal structure necessary for its long term stability.

The following examples are presented to further illustrate and explain the present invention and should not be viewed as limiting in any regard. Unless otherwise indicated, all parts and percentages are by weight, and are based on the weight of the product at the particular stage in processing indicated.

EXAMPLE 1

Reduced calorie fat mixtures are prepared by interesterifying hydrogenated soybean oil (hydrogenated at 180° C. and 60 lbs hydrogen until the Iodine value (IV) is $\leq 3$) with triacetin and tripropionin. A Mettler dropping point (M.D.P.) is determined for each mixture using a Mettler Thermosystem FP 800 following A.O.C.S. Method Cc 18-80 (1989). A solid fat index (S.F.I.) is obtained using A.O.C.S. Method Cd 10-57 (1989). Each mixture is subjected to proton nuclear magnetic resonance (NMR) spectroscopy; integration of the intensities of the various groups gives an estimate of the molar ratio of short (this this case, butyric) to long acids (S/L) present.

One molar equivalent hydrogenated soybean oil (899 g) and 1 molar equivalent of triacetin and tripropionin are interesterified in the presence of 0.2 to 0.3% sodium methoxide by heating to ~110° C with agitation under a vacuum for about half an hour until color develops. (The M.D.P. may be checked at this time, and the reaction continued if the M.D.P. has not dropped sufficiently). Phosphoric acid (~0.2 to ~0.5%, at least twice the amount of sodium methoxide) is added to stop each reaction and neutralize the mixture, followed by the addition of 0.5% activated bleaching clay (Tonsil Optimum FF), 0.5% diatomaceous earth, and 1000 ppm citric acid (dissolved in water) to decolorize and remove soaps. The treatment is continued for ½ to 1 hour at 110° C. The products are cooled to 80° C., filtered, bleached, and steam deodorized at 210° C for 2 to 3 hours.

EXAMPLE 1a

The low calorie triglyceride mixture prepared according to the process of Example 1, is infused into defatted peanuts by the following procedure:

224 pounds of blanched full-fat peanuts are pressed in a vertical press under pressures which were raised to a maximum of 1500 psi with the press cycles which average (from fill to discharge) of 1 hour. Fifty-six pounds of oil is pressed out of the peanuts, leaving 168 pounds of defatted nuts. The defatted nuts are then steam reconstituted.

100 pounds of the defatted nuts are fed to an Odenberg/double cone blender, which is rotated through the entire process. Nine percent of the low calorie triglyceride material of Example 1 is added to the blender and a vacuum of approximately 29-30 in. Hg. applied and held for 12 minutes. The pressure is then released and the infused nuts held for about one hour.

The resulting nuts are found to have a crunch and mouthfeel similar to that of full-fat nuts.

EXAMPLE 2

Reduced calorie fat mixtures are prepared by interesterifying hydrogenated soybean oil (hydrogenated at 180° C. and 60 lbs hydrogen until the Iodine Value (IV) is ≦3) with tributyrin (obtained commercially from Eastman Kodak). A Mettler dropping point (M.D.P.) is determined for each mixture using a Mettler Thermosystem FP 800 following A.O.C.S. Method Cc 18-80 (1989). A solid fat index (S.F.I.) is obtained using A.O.C.S. Method Cd 10-57 (1989). Each mixture is subjected to proton nuclear magnetic resonance (NMR) spectroscopy; integration of the intensities of the various groups gives an estimate of the molar ratio of short (in this case, butyric) to long acids (S/L) present.

One molar equivalent hydrogenated soybean oil (899 g) and 2.5 molar equivalents tributyrin are interesterified in the presence of 0.2 to 0.3% sodium methoxide by heating to ~110° C. with agitation under a vacuum for about half an hour until color develops. (The M.D.P. may be checked at this time, and the reaction continued if the M.D.P. has not dropped sufficiently). Phosphoric acid (~0.2 to ~0.5%, at least twice the amount of sodium methoxide) is added to stop each reaction and neutralize the mixture, followed by the addition of 0.5% activated bleaching clay (Tonsil Optimum FF), 0.5% diatomaceous earth, and 1000 ppm citric acid (dissolved in water) to decolorize and remove soaps. The treatment is continued for ½ to 1 hour at 110° C. The products are cooled to 80° C., filtered, bleached, and steam deodorized at 210° C. for 2 to 3 hours.

EXAMPLE 2a

The low calorie triglyceride material prepared according to Example 2 is fractionated in order to separate a liquid fraction and a solid hardstock fraction. The liquid fraction is then recovered for use in forming a nut butter product.

EXAMPLE 2b

A nut butter product is prepared using the low calorie triglyceride materials of Examples 2 and 2a according to the following procedure:

A blender is charged with 10.47 pounds of defatted peanut flour which has a fat level of about 15%, and 31.4 pounds of defatted peanut flour which has a fat level of 32%. To the peanut flour is added 15.7 pounds of polydextrose, 10.47 pounds of non-fat dry milk, 5.23 pounds of sugar, and 0.79 pounds of salt, and the components mixed together. Melted together at 65° C. are 9.42 pounds of the low calorie triglyceride material of Example 2, 13.61 pounds of the low calorie triglyceride material of Example 2b and 2.91 pounds of Durasorb D, which is added to the dry mix at 65° C. and blended completely. Mixing is continued and the product ground and then quiescently cooled until a consistent, spreadable peanut butter product is obtained.

The resulting nut butter product is found to have the consistency and viscosity of commercially available spreadable peanut butter products.

Although the invention has been described in detail for the purpose of illustration, it is understood that such detail is solely for that purpose, and variations can be made therein by those skilled in the art without departing from the spirit an scope of the invention which is defined by the following claims.

What is claimed:

1. A process for producing low calorie nuts with the organoleptic character of full fat nuts comprising:
    a) providing raw nuts which have had at least some of the oil removed therefrom so that they are partially defatted;
    b) contacting the partially defatted nuts with a low calorie triglyceride material which comprises a triglyceride bearing one long chain fatty acid residue and two short chain fatty acid residues, whereby the low calorie triglyceride material is absorbed into the roasted nuts; and
    c) roasting the partially defatted nuts.

2. A process according to claim 1, wherein said long chain fatty acid residues have 16 to 40 carbons and said short chain fatty acid residues having 2 to 5 carbons, said low calorie triglyceride material being essentially trans-free using American Oil Chemists' Society Method Cd 14161 and having the following physical properties:

a Mettler Drop point of about 29° C. to 41° C. using American Oil Chemists' Society Method Cc 9a-48;
　　a smoke point of no less than about 250° F. using American Oil Chemist's Society Method Cc 91-48;
　　a flash point of no less than about 420° F. using American Oil Chemist's Society Method 9a-48;
　　a fire point of no less than about 420° F. using American Oil Chemist's Society Method 91-48;
　　a refractive index at 60° C. of about 1.4250 to 1.4770 using American Oil Chemist's Society Method Cc 7-25;
　　a saponification value of at least about 170 using American Oil Chemist's Society Method 3-25;

an oxidation stability using American Oil Chemist's Society Method Cd 12-57 of at least about 270 hours;

a free fatty acid value of about 0.20 to about 0.6 using American Oil Chemist's Society Method 5a-40;

an a solid fat content of at least about 35% at 50° F., at least about 20% at 70° F., about 5% to about 40% at 80° F., about 2% to about 25% at 92° F., and about 0 to about 15% at 100° F. using American Oil Chemist's Society Method Cd 16-81;

a viscosity of about 25 to about 42 cps at 100° F. and about 14 to about 23 cps at 150° F.; and essentially no crystals exceeding 8μ observed on microscopic examination under polarized light.

3. A process according to claim 1, wherein said low calorie triglyceride material comprises at least two triglycerides of the following formulae

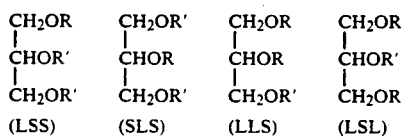

(LSS)  (SLS)  (LLS)  (LSL)

wherein
each R, independently, is a long chain saturated fatty acid residue having between 18 and 22 carbons,
each R', independently, is a short chain acid residue having 2 to 4 carbons derived from fatty acids selected from the group consisting of propionic acid, butyric acid, and combinations of these with each other and with acetic acid, wherein said mixture contains at least about 75% by weight SSL and SLS species and between about 0.1 and about 25% by weight LLS and LSL species.

4. A process according to claim 1, wherein said low calorie triglyceride material is derived by the interesterification of a substantially hydrogenated fat having at least about 75% stearic acid residues, based on the weight of the fatty acids, with one or more triglycerides selected from the group consisting of triacetin, tripropionin, and tributyrin.

5. A process according to claim 4, wherein the hydrogenated fat is selected from the group consisting of hydrogenated canola and hydrogenated soybean oil.

6. A process according to claim 1, wherein the low calorie triglyceride material is present during said contacting in an infusion liquid which further comprises a liquid triglyceride fat.

7. A process according to claim 1, wherein the low calorie triglyceride material is present during said contacting in an infusion liquid which consists essentially of the low calorie triglyceride material.

8. A process according to claim 1, wherein the roasted, partially defatted nuts have a moisture content of less than 3% and are roasted to a color level of 60 to 95 measured on an Agtron color photometer employed in the green mode with 12% and 33% plates defining the reading scale.

9. A process according to claim 1, wherein the low calorie triglyceride material is present during said contacting in an infusion liquid which further comprises additives selected from the group consisting of vitamins, flavoring agents, and sweeteners.

10. A nut produced according to the process of claim 2.

* * * * *

UNITED STATES PATENT AND TRADEMARK OFFICE
CERTIFICATE OF CORRECTION

PATENT NO. : 5,240,726

DATED : August 31, 1993

INVENTOR(S) : Denise Zook, et al

It is certified that error appears in the above-indentified patent and that said Letters Patent is hereby corrected as shown below:

At Col. 7, Line 24, delete "($21.1°$, $80°F.(26.7°)$, $92°F.(33.3°)$)," and substitute therefor --($21.1°C.$, $80°F.$ $(26.7°C.)$, $92°F.$ $(33.3°C.)$,--

At Col. 9, Line 33, delete "mixture" and substitute therefor --mixtures--.

At Col. 9, Line 35, delete "1.3-distearoyl" and substitute therefor --1,3-distearoyl--.

At Col. 9, Line 47, delete "2.3-distearoyl" and substitute therefor --2,3-distearoyl--.

At Col. 10, Line 15, delete "$(CH_2)_{14}$" and substitute therefor --$(CH_2)_4$--.

At Col. 11, Line 51, delete "-(C-" and substitute therefor -- -(CO)- --.

UNITED STATES PATENT AND TRADEMARK OFFICE
CERTIFICATE OF CORRECTION

PATENT NO. : 5,240,726

DATED : August 31, 1993

INVENTOR(S) : Denise Zook, et al

It is certified that error appears in the above-indentified patent and that said Letters Patent is hereby corrected as shown below:

At Col. 11, Line 52, delete "))-".

At Col. 19, Line 45, insert --deoderizing.-- immediately after "steam".

At Col. 22, Line 34, delete "an" and substitute therefor --and--.

At Col. 22, Line 54, delete "14161" and substitute therefor --14-61--.

Signed and Sealed this

Fourteenth Day of June, 1994

Attest:

BRUCE LEHMAN

Attesting Officer    Commissioner of Patents and Trademarks